United States Patent [19]

Witzel

[11] Patent Number: 4,628,925
[45] Date of Patent: Dec. 16, 1986

[54] QUICK-RELEASE LIMB HOLDER APPARATUS

[75] Inventor: Marshall Witzel, Wilmette, Ill.

[73] Assignee: Heelbo, Inc., Niles, Ill.

[21] Appl. No.: 832,576

[22] Filed: Feb. 24, 1986

[51] Int. Cl.⁴ .............................................. A61F 13/00
[52] U.S. Cl. ..................................... 128/133; 128/134
[58] Field of Search ..................... 128/133–135, 128/686, 80 R, DIG. 15; 2/16, 161 A, 161 R, 338, 170, 162; 24/306, 197

[56] References Cited

U.S. PATENT DOCUMENTS

| | | | |
|---|---|---|---|
| 1,551,932 | 9/1925 | Carver | 128/134 X |
| 1,596,792 | 8/1926 | Barry et al. | 128/134 |
| 2,245,293 | 6/1941 | Ogborn | 128/134 |
| 2,559,788 | 7/1951 | Patterson, Jr. | 2/162 |
| 2,706,477 | 4/1955 | Daake | 128/134 |
| 2,858,542 | 11/1958 | Ogg | 2/161 A |
| 2,998,008 | 8/1961 | Klesa | 128/133 |
| 3,027,895 | 4/1962 | Williams | 128/133 |
| 3,247,843 | 4/1966 | Callahan | 128/134 |
| 3,297,026 | 1/1967 | Van Pelt | 128/133 |
| 3,535,718 | 10/1970 | Murcott | 128/133 |
| 3,543,977 | 12/1970 | Lockridge | 128/DIG. 15 X |
| 3,939,829 | 2/1976 | Spann | 128/133 |
| 4,204,534 | 5/1980 | Leary | 128/134 |
| 4,414,969 | 11/1983 | Heyman | 128/133 |

Primary Examiner—Robert A. Hafer
Assistant Examiner—Kathleen J. D'Arrigo
Attorney, Agent, or Firm—Dick and Harris

[57] ABSTRACT

A quick-release limb holder apparatus for releasable affixation about a patient's limb to secure the patient, as desired, to an affixed object, such as a hospital bed, in order to immobilize the patient. An adjustable and independently separable series of straps encircles the patient's limb in a manner which permits the patient to be quickly freed from a restrained position within the apparatus without necessitating the complete disassembly of adjustment straps as well as obviates the need for readjustment of the straps upon reaffixation of the apparatus about the patient's limb. A cuff is interposed between the encircling straps and the patient's skin to cushion and insulate the patient's limb from forces exerted by the encircling straps to thereby minimize any potential for abrasion, irritation or other discomfort.

14 Claims, 12 Drawing Figures

QUICK-RELEASE LIMB HOLDER APPARATUS

BACKGROUND OF THE INVENTION

The present invention relates generally to patient restraint devices and, in particular, to a quick-release limb holder apparatus for independent release, alternative adjusting and releasable affixation about a patient's limb in a manner which permits the patient to be freed from the apparatus without necessitating its complete disassembly.

Over time, a number of apparata have been addressed to securing a patient in an immobile position or otherwise limit a patient's mobility by way of securing one or more of the patient's limbs to a fixed object such as a bedpost or other similar fixture. Such prior art devices typically comprise a single strap which encircled a patient's limb. A buckle or other fastening device would typically be provided for adjusting the encircling strap so that it fits snugly against the patient's limb. Interposed between the typically adjustable encircling strap and the patient's limb has been a foam pad designed to cushion the patient's limb from the abrasive effects of the surrounding strap and buckle.

Unfortunately, however, many of such prior art limb holder apparatus have experienced drawbacks which complicate their usage and on occasion can result in injury to the patient sought to be restrained as well as substantial inconvenience to attending personnel seeking to position said limb holder apparatus upon the patient and in turn about the fixed object, such as a hospital bed, to which the patient is restrained. These prior art devices typically employ a single strap circling the patient's limb in an uninterrupted fashion, the free end of which would be secured to the fixed object. In order to release the patient from the limb holder, the attending personnel had to first detach the free end of the strap from the fixed object and completely separate the strap from the buckle to remove the apparatus. Such a complicated removal operation can be both time consuming and potentially dangerous as the patient, during this "removal" time period is held in only partial restraint while the buckle and strap have to be separated. A patient possessing violent tendencies could, under such circumstances, be provided with the opportunity to somehow injure himself or his attending personnel. These same dangers, both to the patient and attending personnel are present when such prior art limb holder apparatus are sought to be repositioned about the patient's limbs. An additional and potentially more dangerous condition may exist regarding the use of conventional prior art limb holder apparatus where a restrained patient who may need sudden and/or emergency care must first be freed from said limb holder apparatus, a relatively time-consuming, cumbersome process which can potentially delay the application of the needed emergency treatment thus unduly endangering the patient's health.

Accordingly, it is an object of the present invention to provide a quick-release limb holder for releasable affixation about a patient's limb to secure a patient, as desired, to a fixed object, such as a hospital bed frame or rail, in a manner which permits the patient to be freed from the apparatus in an efficient quick manner without necessitating the complete disassembly of the limb holder apparatus.

It is additionally an object of the present invention to provide a quick-release limb holder which is easily adjustable to conform to different size limbs.

It is a further object of the present invention to provide such a quick-release limb holder which utilizes quick-release coupling elements which can alternatively provide for the complete encirclement of the patient's limb and provide for the efficient interruption of said encirclement, all without necessitating the complete disassembly of the limb holder apparatus.

It is yet another object of the invention to provide such a limb holder apparatus constructed of washable and rustproof materials which are capable of effectively withstanding the repeated cleansing and sterilization of the quick-release limb holder apparatus.

Another object of the present invention is to provide such a quick-release limb holder apparatus which utilizes a cuff interposed between the patient's skin and the encircling straps which serves to cushion and insulate the patient's limb from the abrasive effects of all the surrounding straps and fittings. This cuff is constructed of a quilted material having seamless edges which serve to improve the exposure of air to the patient's skin covered by the cuff and further prevent the risk of abrasion to the patient's limb.

These and other objects of the invention will become apparent in light of the present specification and drawings.

SUMMARY OF THE INVENTION

The present invention comprises a quick-release limb holder apparatus for releasable and adjustable affixation about a patient's limb to secure the limb and, in turn, the patient, as desired, to a fixed object in order to immobilize or otherwise restrict the patient's movement. The apparatus functions in a manner which permits the patient to be freed from the apparatus without necessitating the complete disassembly of the apparatus and without requiring its readjustment upon reaffixation about the patient's limb. The quick-release limb holder apparatus itself comprises first strap means, second strap means, adjustment means, and quick-release coupling means all of which combine to encircle a patient's limb and anchor the encircled limb to a given fixed object.

The first strap means has a first end and a second end where the first end is capable of being releasably secured to a fixed object, such as a bedpost or other anchoring means. A portion of the first strap means serves to partially encircle the patient's limb. An adjustment means is provided which is adjustably positionable along a portion of the length of the first strap means which serves to alternatively increase or decrease the length of that portion of the first strap means encircling the patient's limb. The adjustment means thus permits the limb holder apparatus to conform to varied size limbs in order to effectively secure said limb. A second strap means is provided which has a first end and a second end where the first end is operably attached to the adjustment means. The second strap means serves to further encircle the patient's limb.

A quick-release coupling means is provided which includes a first attachment member operably attached to the second end of the first strap means, a second attachment member operably attached to the second end of the second strap means and a detachable coupling member operably interposed between the first and second attachment members. The detachable coupling member is capable of alternatively affixing and releasing the portion of the first and second attachment members relative to one another to alternatively connect and disconnect the first strap means to the second strap means, to, in turn, alternatively complete and release the entire encirclement of the patient's limb, to alternatively permit and release the restraint of said patient's limb. This serves to quickly affix and release the patient's limb from the apparatus in a facilitated manner without the need to release and readjust the adjustment means upon removal and reaffixation of the apparatus upon the patient's limb.

A cuff means is operably interposed between the limb of the patient and the inner facing surfaces of the first strap means, second strap means, adjustment means and quick-release coupling means, and the surface of the patient's limb encircled thereby. The cuff means serves to cushion and insulate the patient's limb from the constrictive and abrasive forces which, due to the patient's movement, are exerted by the encircling first and second strap means, adjustment means and quick-release coupling means upon the patient's limb. Such forces are of particular concern should the patient struggle to free himself from the apparatus and yet are still present as the patient quietly moves about. The cushioning and insulation provided by the cuff means serves to minimize any abrasion, irritation or other discomfort which would otherwise be inflicted upon said patient's limb by the encircling strap means, adjustment means and quick-release coupling means.

In the preferred embodiment, the cuff means is operably affixed to a portion of the inner facing surface of each of the first strap means and second strap means. This affixation serves to facilitate and maintain the alignment of the cuff means between the first and second strap means and the patient's limb.

In one embodiment the adjustment means comprise a self-locking buckle member which is operably attached to the first end of the second strap means. This self-locking buckle member accepts the interwinding of at least a portion of the first strap means so as to restrainably yet adjustably lock the first strap means therewithin. The repositioning of the first end of the second strap means along the length of the first strap means serves to fix the length of the first strap means which encircles the patient's limb. Such adjustment permits the limb holder apparatus to effectively secure different size limbs under desired various restraint pressures.

In another embodiment of the invention, the attachment means comprise a pair of substantially D-shaped rings which are operably attached to the first end of the second strap means. These D-shaped rings similarly accept the interwinding of at least a portion of the first strap means to restrainably and yet adjustably lock the first strap means therebetween. Such repositioning similarly serves to fix the length of the first strap means which encircles the patient's limb so as to permit the limb holder apparatus to effectively secure different size limbs.

The first attachment member of the quick-release coupling means comprises an attachment ring which is operably attached to the second end of the first strap means. The second attachment member of the quick-release coupling means comprises a locking ring operably attached to the second end of the second strap means and the detachable coupling member having a first and second end comprises a spring clip member operably and fixedly attached at its first end to the attachment ring and releasably affixed at its second end to the locking ring. The spring clip member is capable of alternatively affixing and releasing the position of the attachment ring relative to the locking ring to alternatively connect and disconnect the first and second strap means, to, in turn, alternatively form and release the entire encirclement of the patient's limb by the first and second strap means, adjustment means and quick-release coupling means. This serves to alternatively permit and release the restraint about the patient's limb. In operation, the apparatus is placed about the patient's limb and the quick-release coupling means is engaged so as to completely encircle the patient's limb. Once done, the apparatus is adjusted via the adjustment means to form an effective and secure fitment about the patient's limb. Finally, the free end of the first strap means is fastened to the fixed object, such as the bedpost, to thus secure the patient. The interruption in the encirclement of the patient's limb as provided by the coupling means thus permits the removal of the limb holder apparatus from the patient's limb without necessitating the removal of the first end of the first strap means from its anchored position and further permits the limb holder apparatus to be repositioned about the patient's limb in a prompt and efficient manner and without necessitating reposition of the adjustment means along the first strap means.

In another embodiment of the invention, the first attachment member of the quick-release coupling means comprises one or more female snap fasteners operably attached to the second end of the first strap means, the second attachment member of the quick-release coupling means comprises one or more male snap fasteners operably attached to the second end of the second strap means. The detachable coupling member of the quick-release coupling means comprises alignable telescopically mated fastening elements on both of said male and female snap fasteners for restrained yet releasable affixation therebetween. The fastening elements are capable of alternatively affixing and releasing the portion of the female snap fasteners relative to the male snap fasteners to, alternatively, connect and disconnect the first and second strap means, to, in turn, alternatively form and release the entire encirclement of the patient's limb by the first and second strap means, adjustment means and quick-release coupling means. This arrangement serves to alternatively permit and release the restraint of the apparatus about the patient's limb.

In the preferred embodiment of the invention, the cuff means is of a substantially rectangular shape having a first and second end and is of such a length so as to cause the first and second ends of the cuff means to overlap one another when the cuff means is positioned so as to encircle the patient's limb. Furthermore, the overlapped portion of the cuff means is preferably positioned proximate to the quick-release coupling means in order to provide additional cushioning and insulation for the patient's limb in the area directly beneath the quick-release coupling means. The cuff means further comprises a cuff attachment means which is capable of retaining the cuff means in the substantially overlapped orientation about the patient's limb. This cuff attachment means permits the cuff means to effectively conform to different size limbs and, further, temporarily restrain the patient's limb to accordingly facilitate the operation of the quick-release coupling means. In preferred embodiment of the invention, the cuff attachment means comprises a hook and loop fastener where the hook portion of the fastener is attached to at least a portion of the exterior facing surface of the first end of the cuff means and the loop portion is attached to at least a portion of the inner facing surface of the second end of the cuff means, each preferably being sewn to the cuff means. The hook and loop portions of said fastener thus engage one another when the cuff means is in a substantially overlapped position about the patient's limb.

The strap means of the present invention are preferably fabricated of a washable, woven, cotton material in order to minimize abrasion and other discomfort should the straps ever contact the patient's skin. This construction further permits the cleansing and sterilization of the quick-release limb holder apparatus without risk of its deterioration due to cleansing and sterilization process. The cuff means is preferably fabricated of a washable polyurethane core which is laminated with a washable triacetate fabric which serves to cushion and insulate the limb from the encircling strap means, adjustment means and coupling means. This particular fabrication permits the cleansing and sterilization of the quick-release limb holder apparatus, all without risk of its deterioration. In order to further facilitate effective cleansing and sterilization, the adjustment means and quick-release coupling means are preferably fabricated of a substantially rustproof material capable of withstanding the cleansing and sterilization process.

The cuff means of the preferred invention is preferably quilted to provide ventilation permitting oxygen to reach the patient's skin covered by the cuff means and prevent the build up of heat or other discomfort associated with the covering of the patient's skin. This cuff means is additionally preferably configured so as to have seamless edges, so as to further minimize any abrasive effect upon the patient's limb.

DETAILED DESCRIPTION OF THE DRAWINGS

Figure 1:
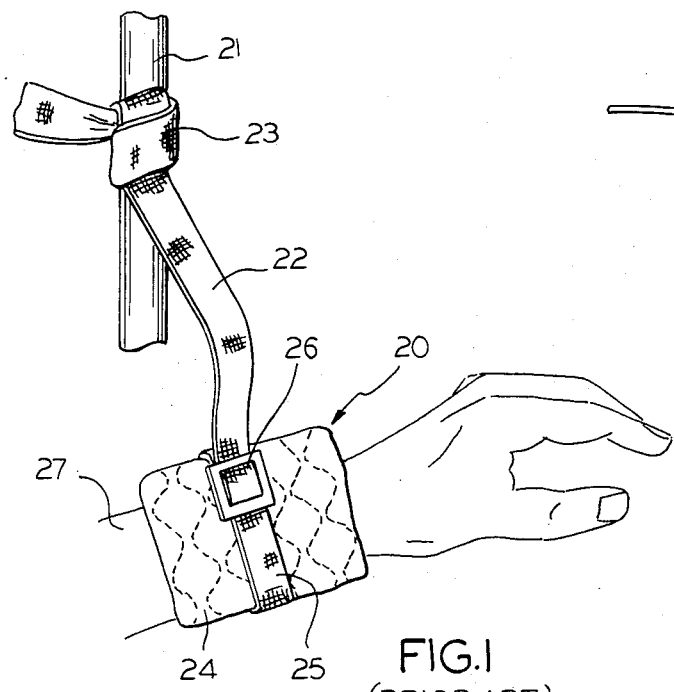
FIG. 1 of the drawings is an elevated side view of a prior art limb holder construction, with conventional strap, buckle and cushioning pad, the strap being shown secured to a post such as a bedpost.

While this invention is susceptible of embodiment in many different forms, there is shown in the drawings and will herein be described in detail, several specific embodiments, with the understanding that the present disclosure is to be considered as an exemplification of the principles of the invention and is not intended to limit the invention to the embodiment illustrated.

FIG. 1 through FIG. 4 set forth the prior art that has been used in association with limb holder apparata, specifically the manner in which a patient's limb is encircled by a single uninterrupted strap and adjustments which may be made thereto. FIG. 1 shows one prior art limb holder 20 positioned about a patient's arm 27. A single strap 22 is used to secure arm 27 to a fixed object 21 with a portion of strap 22, designated 25, encircling limb 27. The free end of strap 22 is shown secured to fixed object 21, such as a bedpost, by way of knot 23. Positioned between the encircling strap 25 and patient's limb 27 is a cushion 24 designed to minimize any abrasion to limb 27 as a result of encircling strap 25. The encircling portion 25 of strap 22 can be adjusted by way of buckle 26 such that strap portion 25 fits snugly and securely around patient limb 27.

Figure 2:
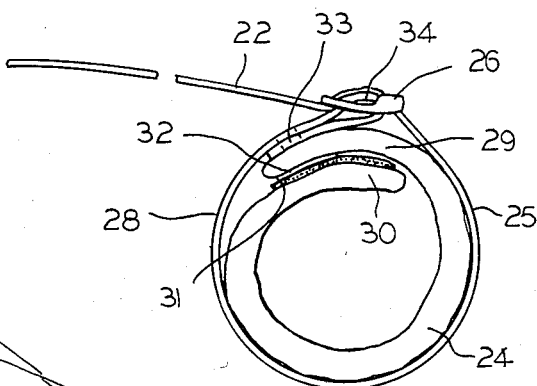
FIG. 2 of the drawings is an elevated front view of the prior art limb holder of FIG. 1 illustrating the complete uninterrupted encirclement by a single strap threaded through a conventional adjusting buckle.

FIG. 2 shows an elevated front view of the prior art device shown in FIG. 1. While not illustrating the free end of strap 22 being secured to a fixed object, strap 22 is shown passing through adjustment buckle 26 after completely encircling in an uninterrupted manner the space provided for patient's limb. Encircling strap 25 is shown attached to cushion end 29 of cushion 24 by way of stitching 33. The remaining portion of cushion 24 remains free and unattached to encircling strap 25. Cushion end 30 is shown being overlapped by cushion end 29 and held in such position by way of hook and loop fasteners 31 and 32 respectively.

Figure 3:
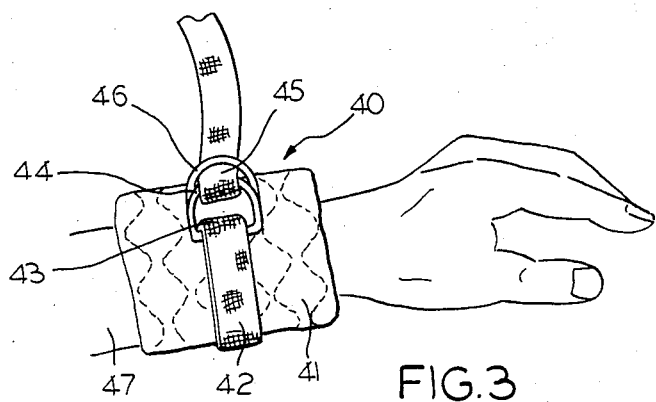
FIG. 3 of the drawings is an elevated side view of another prior art limb restraint apparatus utilized in the prior art, in which conventional D-shaped buckles accept the interwinding of the single strap for uninterrupted complete encirclement of a patient's limb.

A similar prior art limb holder is shown in FIG. 3 wherein strap 45 passes through adjustment buckles 44 and 46 encircling patient limb 47 in a similar uninterrupted fashion.

Figure 4:
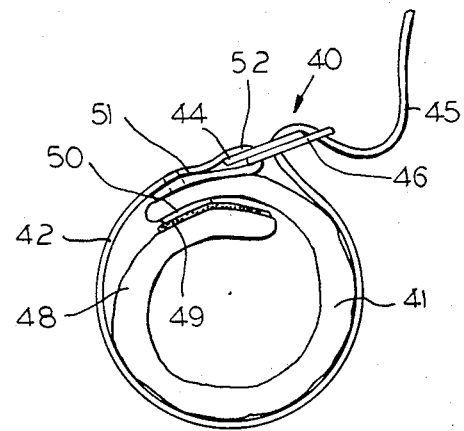
FIG. 4 of the drawings is an elevated front view of the prior art limb holder of FIG. 3 illustrating complete uninterrupted encirclement by the single strap threaded through a D-Ring adjustment buckle.

FIG. 4 shows an elevated front view of the prior art device 40 shown in FIG. 3. Strap 45 is shown making a complete uninterrupted encirclement as does the prior art device shown in FIG. 1 and FIG. 2 which similarly requires that the free end of strap 45 be detached from its anchored object and completely separated from buckles 44 and 46 to free the apparatus from the patient's limb.

Figure 5:
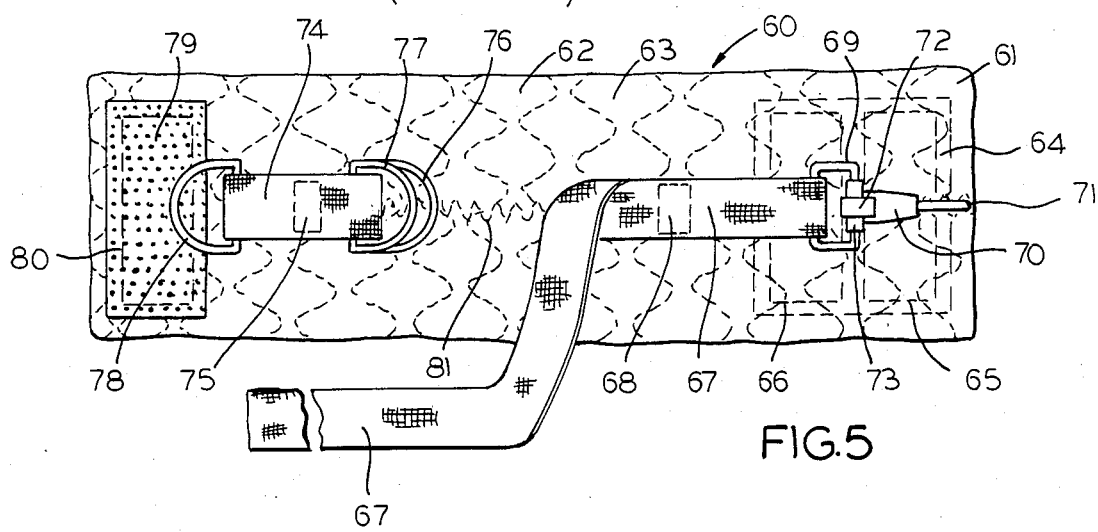
FIG. 5 of the drawings is a top plan view of the unattached quick-release limb holder apparatus of the present invention in which the first strap means, second strap means, attachment means and quick-release coupling means are shown, together with the cuff means and cuff attachment means.

The present invention, quick-release limb holder apparatus 60 is shown in FIG. 5 in its open unassembled position. The first end of first strap means 67 is typically secured to a fixed object by tying the first strap means thereto (not shown). The first end of second strap means 74 is shown operably attached to adjustment means 76 and 77. Quick-release coupling means 70 is shown attached to the second end of first strap means 67. In a preferred embodiment illustrated, coupling means 70 comprises attachment ring 69, spring clip 71 and locking ring 78. The engagement of spring clip 71 with locking ring 78 serves to attach the second end of first strap means 67 to the second strap means 74. Spring clip 71 is shown further comprising fittings 72 and 73 which permit spring clip 71 to better conform to the shape of the patient's limb. In this preferred embodiment, the adjustment means are shown comprising D-shaped buckles 76 and 77 which are attached to the first end of second strap means 74.

Cuff means 61 is shown comprising a substantially rectangular shaped piece of cushioning material which is interposed between first strap means 67, second strap means 74, adjustment means 76 and 77 and quick-release coupling means 70, and the patient's skin so as to insulate and cushion the patient's limb. Cuff means 61 is attached to first strap means 67 and second strap means 74 by way of stitching 68 and 75, respectively. Cuff attachment means 64 and 79 are shown attached to portions of opposing surfaces of cuff means 61. These cuff attachments means are held in place by way of stitching 65, 66 and 80. In the preferred embodiment illustrated, cuff means 61 is shown including quilting represented by designations 62 and 63, and further includes a centrally positioned seam 81 to provide smooth seamless edges.

Figure 6:
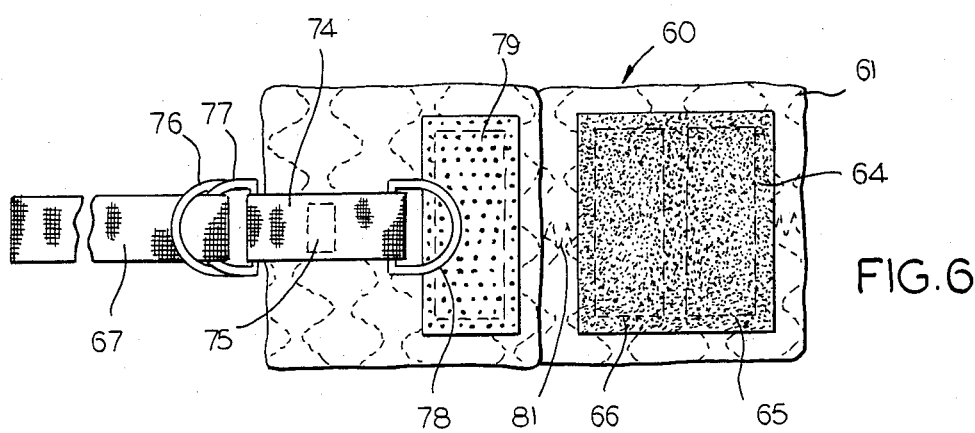
FIG. 6 of the drawings is a top plan view of the quick-release limb holder apparatus shown with the cuff means in a partially overlapped (encircling) position, the attachment of the first and second strap means to the adjustment means, and specifically showing a portion of the quick-release coupling means, in the alternative uncoupled position.

FIG. 6 shows quick-release limb holder apparatus 60 in a partially assembled position. First strap means 67 is shown interwound through attachment means 76 and 77 which are in turn attached to second strap means 74. Locking ring 78 and spring clip 71 of quick-release coupling means 70 are shown detached from one another such that the encirclement about the patient's limb is broken permitting quick-release limb holder apparatus 60 to be quickly and easily removed from about the patient's limb, not shown.

Figure 7:
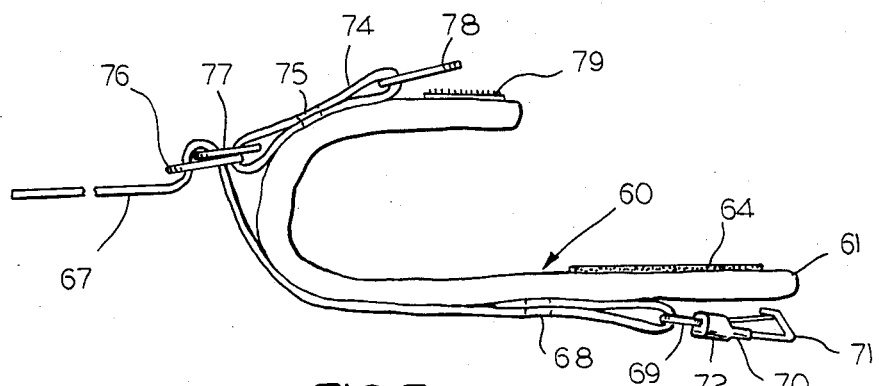
FIG. 7 of the drawings is an elevated front view of the limb holder apparatus of FIG. 6 specifically showing the partial uninterrupted encirclement of the apparatus occurring when the coupling means in its alternative uncoupled position.

FIG. 7 shows an elevated front view of limb holder apparatus 60. It can be clearly seen that the encirclement of the patient's limb formed by first strap means 67, second strap means 74, attachment means 76 and 77 and quick-release coupling means 70 can be alternatively completed by the engagement of spring clip 71 and locking ring 78 and interrupted by the disengagement of spring clip 71 and locking ring 78. First strap means 67 is shown interwound through adjustment buckles 76 and 77 which serve to determine the length of first strap means 67 which is capable of encircling the patient's limb. By repositioning and fixing buckles 76 and 77 along the length of first strap means 67, limb holder apparatus 60 may be adjusted snugly about the patient's limb. The alternative engagement and disengagement of quick-release coupling means 70 permits limb holder apparatus 60 to be removed or reinstalled upon the patient's limb without necessitating the complete disassembly of limb holder apparatus 60 as the free end of first strap means 67 can remain fixed at all times, unlike the prior art devices shown in FIG. 1 through FIG. 4.

Figure 8:
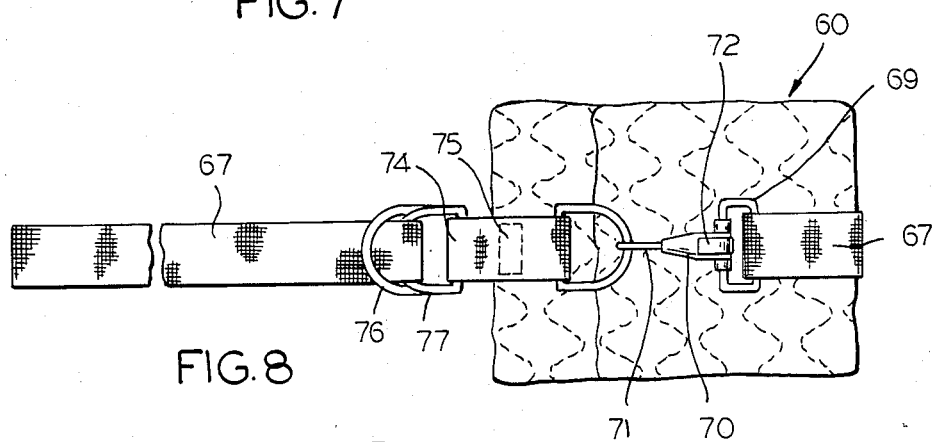
FIG. 8 of the drawings is a top plan view of the quick-release limb holder apparatus shown with the quick-release coupling means in its alternate coupled position.

FIG. 8 shows a top plan view of an assembled quick-release limb holder apparatus 60 wherein spring clip 71 is engaged with locking ring 78 so as to form the complete encirclement of the patient's limb. The attachment of cuff means 60 to second strap means 74 by way of stitching 75 and said cuff means 60 to first strap means 67 by way of stitching 68, not shown, serves to automatically align cuff means 60 with the encirclement achieved in part by way of strap means 67 and 74.

Figure 9:
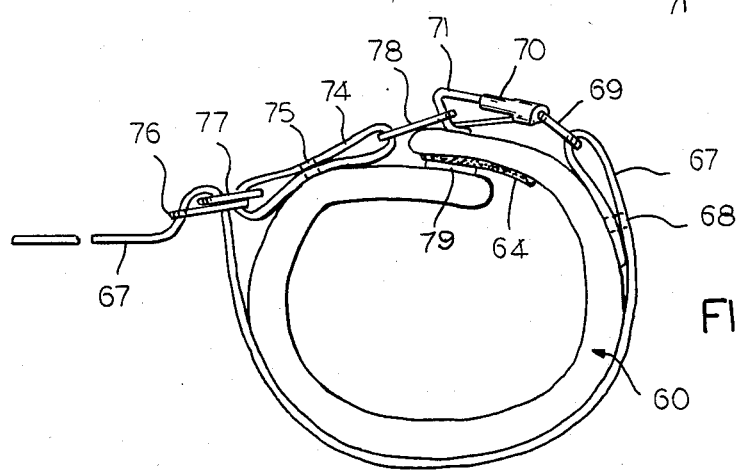
FIG. 9 of the drawings is an elevated front view of the limb holder apparatus of FIG. 8 particularly showing the complete encirclement obtained when the coupling means is in its alternative coupled position and further illustrating the overlap of the cuff means proximate to the coupled coupling means.

FIG. 9 illustrates an assembled quick-release limb holder apparatus 60 wherein spring clip 71 is engaged with locking ring 78. FIG. 9 clearly depicts the complete encirclement achieved by the cooperation of first strap means 67, second strap means 74, adjustment means 76 and 77 and quick-release coupling means 70. Cuff means 60 is shown in an overlap orientation wherein the overlap portion is positioned proximate to quick-release coupling means 70 so as to further cushion and insulate the patient's limb from said quick-release coupling means 70. Cuff attachment means 64 and 79 retain cuff means 60 in its overlap position about a patient's limb. In operation, cuff means 60 is placed about the patient's wrist in an overlapped orientation temporarily held in place by cuff attachment means 64 and 79. This temporary attachment serves to facilitate the cooperation and operation of spring clip 71 and locking ring 78. The adjustment capability of quick-release limb holder 60 is clearly shown to be achieved by the repositioning of adjustment buckles 76 and 77 along a portion of the length of first strap means 67 to effectively fit the apparatus to different size limbs.

Figure 10:
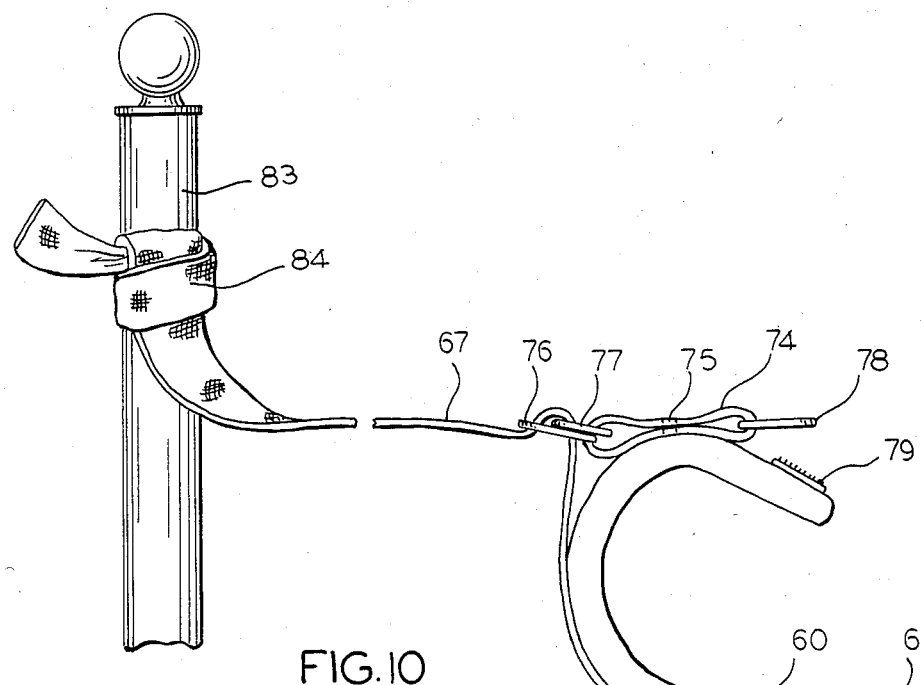
FIG. 10 of the drawings is an elevated side schematic view of the present limb holder apparatus specifically illustrating how the patient's limb may be freed in a facilitated manner from the apparatus without requiring either the release of the adjustment means or its complete disassembly and removal from the anchoring object.

FIG. 10 further illustrates the operation of limb holder apparatus 60 wherein the encirclement about the patient's limb may be broken by the detachment of spring clip 71 from locking ring 78 such that limb holder apparatus 60 may be readily removed from the patient's limb without necessitating the complete disassembly of limb holder apparatus 60, e.g., the detachment of first strap means 67 and knot 84 from the fixed anchoring object 83. In addition, upon reinstallation of limb holder apparatus 60 upon the patient's limb it is shown that first strap means 67 and adjustment buckles 76 and 77 need not be repositioned in order to reaffix quick-release limb holder apparatus 60 about said patient's limb.

Figure 11:
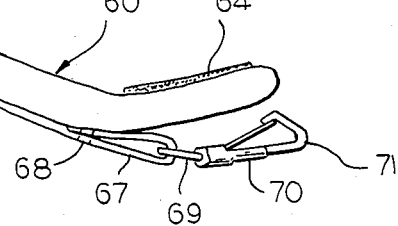
FIG. 11 of the drawings is a top plan view of the quick-release limb holder apparatus showing an alternative embodiment of quick-release coupling means specifically comprising a pair of snap fasteners.
Figure 11:
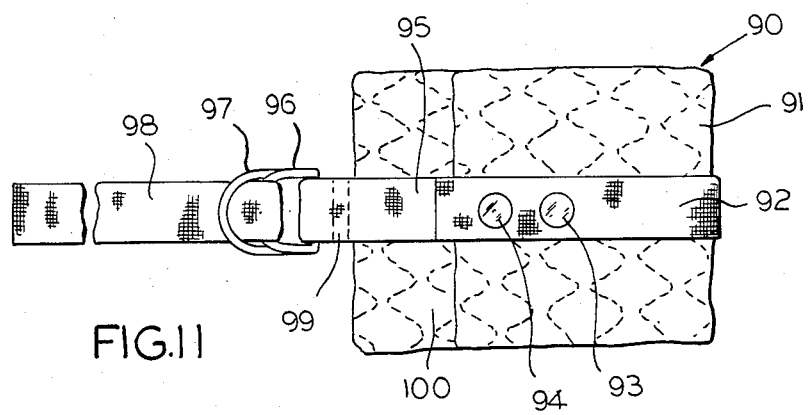
Figure 12:
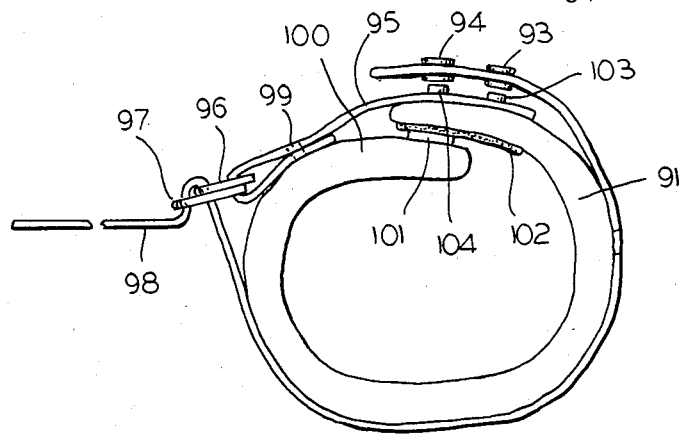
FIG. 12 of the drawings is an elevated front view of the alternative embodiment of FIG. 11 specifically illustrating the engagement of the snap fasteners and corresponding immunity of the snap fasteners to potential shear forces.

FIG. 11 and FIG. 12 illustrate an alternative embodiment of the present invention wherein the coupling means comprise a pair of snap fasteners having female snap fastener portions 93 and 94 and male snap fastener portions 103 and 104. Said respective portions of each snap fastener alternately engage and disengage with one another to, in turn, serve to connect the first strap means 98 to the second strap means 95. As can be seen in FIG. 12, the forces required to be exerted upon said snap fasteners 93 and 94 to disengage same are in an upward direction such that any sheer forces exerted upon said fasteners by first strap means 98 and second strap means 95 are insufficient to disengage said snap fasteners.

The foregoing description and drawings merely explain and illustrate the invention and the invention is not limited thereto, except in so far as the amended claims are so limited as those skilled in the art who have the disclosure before them will be able to make modifications and variations therein without departing from the scope of the invention.

What is claimed is:

1. A quick-release limb holder apparatus for releasable adjustable affixation about a patient's limb to secure the limb, as desired, to a fixed object to thus immobilize the limb and thus the patient in a manner which simultaneously permits said patient to be freed from said apparatus instantaneously, without the complete disassembly of said quick-release limb holder apparatus and without requiring its readjustment upon reaffixation of said apparatus about said patient's limb, said quick-release limb holder apparatus comprising:

first strap means having a first end and a second end, said first end of said first strap means being capable of releasable securement to said fixed object, said first strap means serving to partially encircle said patient's limb;

adjustment means operably positioned about at least a portion of said first strap means to alternatively increase and decrease the length of said first strap means encircling said patient's limb and thus said first strap means fitment about said limb, thereby permitting said limb holder apparatus to conform to the encirclement of varied size limbs;

second strap means having a first end and a second end, said first end of said second strap means operably attached to said adjustment means positioned about said first strap means, said second strap means further encircling said patient's limb;

quick-release coupling means including a first attachment member operably attached to said second end of said first strap means, a second attachment member operably attached to said second end of said second strap means, and a detachable coupling member operably interposed between said first and second attachment members, said detachable coupling member capable of alternatively affixing and releasing the position of said first and second attachment members relative to one another to alternatively connect and disconnect said first strap means to said second strap means, to, in turn, alternatively complete and release the entire encirclement of said patient's limb, to alternatively permit and release the restraint of said patient's limb respectively, thereby quickly affixing and releasing said patient's limb from said apparatus in a facilitated manner without the need to release and readjust said adjustment means upon removal and reaffixation of said apparatus upon said patient's limb;

cuff means operably interposed between the limb of the patient and the inner facing surfaces of said first and second strap means, said adjustment means and said quick-release coupling means encircling said limb, said cuff means serving to cushion and insulate said patient's limb from the constrictive forces exerted by said encircling first strap means, second strap means, adjustment means and quick-release coupling means upon said limb as said patient moves about to thereby minimize irritation and discomfort which would otherwise be inflicted upon said patient's limb by direct contact with said strap means.

2. The invention according to claim 1 in which said cuff means is operably affixed at one or more points to the innermost facing surfaces of each of said first and second strap means respectively to maintain the aligned positioning of said cuff means therebetween said first and second strap means, said adjustment means and said quick-release coupling means, and said patient's limb.

3. The invention according to claim 1 in which said adjustment means comprises a self-locking buckle member operably attached to said first end of said second strap means, said self-locking buckle member accepting the interwinding of at least a portion of said first strap means to restrainably yet adjustably affix said first strap means therewithin thereby fixing the length of said first strap means encircling said patient's limb to thus permit said limb holder apparatus to effectively secure different size limbs under desired various restraint pressures.

4. The invention according to claim 1 in which said adjustment means comprises a plurality of substantially D-shaped rings operably attached to said first end of said second strap means, said D-shaped rings accepting the interwinding of at least a portion of said first strap means to restrainably yet adjustably affix said first strap means therewithin thereby fixing the length of said first strap means encircling said patient's limb to thus permit said limb holder apparatus to effectively secure different size limbs under desired various restrain pressures.

5. The invention according to claim 1 in which said first attachment member of said quick-release coupling means comprises an attachment ring operably attached to said second end of said first strap means, said second attachment member of said quick-release coupling means comprising a locking ring operably attached to said second end of said second strap means, said detachable coupling member of said quick-release coupling means having a first and second end comprising a spring clip member operably and fixedly attached at its first end to said attachment ring and releasably affixed at its second end to said locking ring, said spring clip member being capable of alternatively affixing and releasing the position of said attachment ring relative to said locking ring to alternatively connect and disconnect said first and second strap means, to, in turn, alternatively form and release the entire encirclement of said patient's limb so as to alternatively permit and release the restraint by said first and second strap means, quick-release coupling means and adjustment means about said patient's limb.

6. The invention according to claim 1 in which said first attachment member of said quick-release coupling means comprises one or more female snap fasteners operably attached to the second end of said first strap means, said second attachment member of said quick-release coupling means comprising one or more male snap fasteners operably attached to the second end of said second strap means, said detachable coupling member of said quick-release coupling means comprising alignable telescopically mated fastening elements on both said female and male snap fasteners for restrained yet releasable affixation therebetween, said fastening elements being capable of alternatively affixing and releasing the portion of said female snap fasteners relative to said male snap fasteners to alternatively connect and disconnect said first and second strap means, to, in turn, alternatively form and release the entire encirclement of said patient's limb by said first and second strap means, quick-release coupling means and adjustment means so as to alternatively permit and release the restraint about said patient's limb.

7. The invention according to claim 1 in which said cuff means is of a substantially rectangular shape having a first end and second end, said cuff means dimensioned so as to result in the overlapping of said first end of said cuff means by said second end of said cuff means when said cuff means is positioned so as to encircle said patient's limb, said overlapped portion of said cuff means further positioned proximate to said quick-release coupling means to, in turn, provide additional cushioning and insulation for said patient's limb proximate to said quick-release coupling means.

8. The invention according to claim 7 in which said cuff means further comprises, cuff attachment means capable of retaining said cuff means in a substantially overlapped orientation about said patient's limb thereby permitting said cuff means to effectively conform to different size limbs, and further temporarily restrain said patient's limb to facilitate the operation of said quick-release coupling means.

9. The invention according to claim 8 in which said cuff attachment means comprises a hook and loop fastener, said hook portion of said fastener operably attached to at least a portion of the exterior facing surface of said first end of said cuff means, said loop portion of said fastener operably attached to at least a portion of the inner facing surface of said second end of said cuff means, said hook and loop fastener being capable of alternatively releasing and retaining said portion of said interior and exterior facing surfaces of said cuff means to one another to, in turn, alternatively release and retain said cuff means in an overlaped position about said patient's limb.

10. The invention according to claim 1 in which said strap means are fabricated of washable, woven cotton material so as to minimize abrasion and other discomfort should said straps ever contact said patient's skin and further permit cleansing and sterilization of said quick-release limb holder apparatus without substantial risk of its deterioration.

11. The invention according to claim 1 in which said cuff means is fabricated of a washable polyurethane core laminated with washable triacetate fabric so as to cushion and insulate said limb from said first and second strap means, adjustment means and quick-release coupling means and further permit cleansing and sterilization of said quick-release limb holder apparatus without substantial risk of its deterioration.

12. The invention according to claim 11 in which said cuff means is quilted so as to permit said patient's skin covered by said cuff means to be exposed to the air to, in turn, prevent the build up of heat or other associated discomfort.

13. The invention according to claim 11 in which said cuff means is configured so as to have seamless edges to thus further minimize any abrasive effect upon said patient's limb.

14. The invention according to claim 1 in which said attachment means and said quick-release coupling means are fabricated of a substantially rustproof material so as to effectively withstand cleansing and sterilization of said quick-release limb holder apparatus.

* * * * *